(12) United States Patent
Hossainy et al.

(10) Patent No.: US 6,635,082 B1
(45) Date of Patent: Oct. 21, 2003

(54) RADIOPAQUE STENT

(75) Inventors: Syed F. A. Hossainy, Fremont, CA (US); Steven Wu, Santa Clara, CA (US)

(73) Assignee: Advanced Cardiovascular Systems Inc., Santa Clara, CA (US)

( * ) Notice: Subject to any disclaimer, the term of this patent is extended or adjusted under 35 U.S.C. 154(b) by 239 days.

(21) Appl. No.: 09/753,206

(22) Filed: Dec. 29, 2000

(51) Int. Cl.$^7$ ................................................. A61F 2/06
(52) U.S. Cl. ..................................... 623/1.15; 623/1.34
(58) Field of Search ............................. 623/1.15, 1.34, 623/1.46, 1.1, 1.4, 1.39, 1.49, 900, 910, 920, 921, 925, 926; 606/194, 191; 600/1, 2, 3, 36; 128/898; 427/2.1–2.31; 528/361, 115; 428/412

(56) References Cited

U.S. PATENT DOCUMENTS

| | | |
|---|---|---|
| 3,105,492 A | 10/1963 | Jeckel |
| 3,868,956 A | 3/1975 | Alfidi et al. |
| 3,993,078 A | 11/1976 | Bergentz et al. |
| 4,130,904 A | 12/1978 | Whalen |
| 4,718,907 A | 1/1988 | Karwoski et al. |
| 4,816,339 A | 3/1989 | Tu et al. |
| 4,879,135 A | 11/1989 | Greco et al. |
| 4,892,539 A | 1/1990 | Koch |
| 4,902,289 A | 2/1990 | Yannas |
| 4,986,831 A | 1/1991 | King et al. |
| 5,024,671 A | 6/1991 | Tu et al. |
| 5,037,377 A | 8/1991 | Alonso |
| 5,047,050 A | 9/1991 | Arpesani |
| 5,059,166 A | 10/1991 | Fischell et al. |
| 5,062,829 A | 11/1991 | Pryor et al. |
| 5,078,736 A | 1/1992 | Behl |
| 5,084,065 A | 1/1992 | Weldon et al. |
| 5,100,429 A | 3/1992 | Sinofsky et al. |
| 5,104,403 A | 4/1992 | Brotzu et al. |
| 5,116,360 A | 5/1992 | Pinchuk et al. |
| 5,156,623 A | 10/1992 | Hakamatsuka et al. |
| 5,163,958 A | 11/1992 | Pinchuk |
| 5,174,326 A | 12/1992 | Steinert et al. |
| 5,176,617 A | 1/1993 | Fischell et al. |
| 5,180,366 A | 1/1993 | Woods |
| 5,236,446 A | 8/1993 | Dumon |
| 5,289,831 A | 3/1994 | Bosley |
| 5,302,168 A | 4/1994 | Hess |
| 5,320,100 A | 6/1994 | Herweck et al. |
| 5,356,433 A | 10/1994 | Rowland et al. |
| 5,380,299 A | 1/1995 | Fearnot et al. |
| 5,415,619 A | 5/1995 | Lee et al. |
| 5,443,496 A | 8/1995 | Schwartz et al. |
| 5,449,382 A | 9/1995 | Dayton |

(List continued on next page.)

FOREIGN PATENT DOCUMENTS

| | | |
|---|---|---|
| WO | WO 98/23228 | 6/1998 |

*Primary Examiner*—Gloria M. Hale
(74) *Attorney, Agent, or Firm*—Fulwider Patton Lee & Utecht, LLP

(57) ABSTRACT

A stent or intraductal medical device is provided having radiopaque marker material deposited on the surface of the stent or medical device to assist visualization of the device during implantation. A method for depositing a radiopaque material on an implantable medical device such as a stent is also described. The radiopaque material may be deposited on the medical device by dipping or immersion, or the radiopaque material may be applied to the device using micro-injection or electrodeposition. The radiopaque material may coat the entire surface of the stent, or only a portion of the stent, or it may be applied to cavities or microdepots formed in the outer surface of the medical device. Excess radiopaque material may be removed from the device by centrifugation or shaking, and the radiopaque material may be heated to bond the material to the surface of the device.

30 Claims, 3 Drawing Sheets

U.S. PATENT DOCUMENTS

| | | | |
|---|---|---|---|
| 5,464,450 | A | 11/1995 | Buscemi et al. |
| 5,500,013 | A | 3/1996 | Buscemi et al. |
| 5,571,166 | A | 11/1996 | Dinh et al. |
| 5,607,442 | A | 3/1997 | Fischell et al. |
| 5,609,629 | A | 3/1997 | Fearnot et al. |
| 5,624,411 | A | 4/1997 | Tuch |
| 5,628,786 | A | 5/1997 | Banas et al. |
| 5,632,776 | A | 5/1997 | Kurumatani et al. |
| 5,637,113 | A | 6/1997 | Tartaglia et al. |
| 5,649,951 | A | 7/1997 | Davidson |
| 5,665,114 | A | 9/1997 | Weadock et al. |
| 5,679,400 | A | 10/1997 | Tuch |
| 5,681,345 | A | 10/1997 | Euteneuer |
| 5,685,306 | A | 11/1997 | Davidson |
| 5,690,670 | A | 11/1997 | Davidson |
| 5,693,085 | A | 12/1997 | Buirge et al. |
| 5,700,285 | A | 12/1997 | Myers et al. |
| 5,700,287 | A | 12/1997 | Myers et al. |
| 5,707,385 | A | 1/1998 | Williams |
| 5,711,763 | A | 1/1998 | Nonami et al. |
| 5,713,949 | A | 2/1998 | Jayaraman |
| 5,718,723 | A | 2/1998 | Matsuda et al. |
| 5,725,572 | A | 3/1998 | Lam et al. |
| 5,741,327 | A | 4/1998 | Frantzen |
| 5,776,184 | A | 7/1998 | Tuch |
| 5,779,729 | A | 7/1998 | Severini |
| 5,782,908 | A | 7/1998 | Cahalan et al. |
| 5,782,910 | A | 7/1998 | Davidson |
| 5,800,512 | A | 9/1998 | Lentz et al. |
| 5,824,042 | A | 10/1998 | Lombardi et al. |
| 5,824,049 | A | 10/1998 | Ragheb et al. |
| 5,824,056 | A | 10/1998 | Rosenberg |
| 5,837,008 | A | 11/1998 | Berg et al. |
| 5,873,904 | A | 2/1999 | Ragheb et al. |
| 5,876,433 | A | 3/1999 | Lunn |
| 5,891,108 | A | 4/1999 | Leone et al. |
| 5,919,126 | A | 7/1999 | Armini |
| 5,972,027 | A | 10/1999 | Johnson |
| 5,976,169 | A | 11/1999 | Imran |
| 5,980,566 | A | 11/1999 | Alt et al. |
| 6,010,445 | A | 1/2000 | Armini et al. |
| 6,022,374 | A | 2/2000 | Imran |
| 6,039,757 | A | 3/2000 | Edwards et al. |
| 6,063,101 | A | 5/2000 | Jacobsen et al. |
| 6,120,536 | A | 9/2000 | Ding et al. |
| 6,159,142 | A | 12/2000 | Alt |
| 6,174,326 | B1 * | 1/2001 | Kitaoka et al. ............ 623/1.34 |
| 6,174,330 | B1 * | 1/2001 | Stinson .................... 623/1.34 |
| 6,315,794 | B1 | 11/2001 | Richter |
| 6,355,058 | B1 * | 3/2002 | Pacetti et al. .............. 623/1.15 |
| 6,368,658 | B1 * | 4/2002 | Schwarz et al. ........... 427/2.15 |
| 6,387,978 | B2 * | 5/2002 | Ronan et al. .............. 523/1.15 |
| 6,426,145 | B1 * | 7/2002 | Moroni ..................... 428/412 |

\* cited by examiner

RADIOPAQUE STENT

BACKGROUND OF THE INVENTION

The present invention relates generally to implantable medical devices and to a method for depositing and affixing solids onto implantable medical devices. More particularly, the present invention relates to a radiopaque implantable device, such as a stent, and to a method for depositing and affixing radiopacifiers onto intravascular or intraductal implant devices.

In a typical percutaneous transluminal coronary angioplasty (PTCA) for compressing lesion plaque against the artery wall to dilate the artery lumen, a guiding catheter is percutaneously introduced into the cardiovascular system of a patient through the brachial or femoral arteries and advanced through the vasculature until the distal end is in the ostium. A dilatation catheter having a balloon on the distal end is introduced through the catheter. The catheter is first advanced into the patient's coronary vasculature until the dilatation balloon is properly positioned across the lesion.

Once in position across the lesion, a flexible, expandable, preformed balloon is inflated to a predetermined size at relatively high pressures to radially compress the atherosclerotic plaque of the lesion against the inside of the artery wall and thereby dilate the lumen of the artery. The balloon is then deflated to a small profile, so that the dilatation catheter can be withdrawn from the patient's vasculature and blood flow resumed through the dilated artery. While this procedure is typical, it is not the only method used in angioplasty.

In angioplasty procedures of the kind referenced above, restenosis of the artery often develops which may require another angioplasty procedure, a surgical bypass operation, or some method of repairing or strengthening the area. To reduce the likelihood of the development of restenosis and strengthen the area, a physician can implant an intravascular prosthesis, typically called a stent, for maintaining vascular patency. A stent is a device used to hold tissue in place or to provide a support for a vessel to hold it open so that blood flows freely. Statistical data suggests that with certain stent designs, the restenosis rate is significantly less than the overall restenosis rate for non-stented arteries receiving a PTCA procedure.

A variety of devices are known in the art for use as stents, including expandable tubular members, in a variety of patterns, that are able to be crimped onto a balloon catheter, and expanded after being positioned intraluminally on the balloon catheter, and that retain their expanded form. Typically, the stent is loaded and crimped onto the balloon portion of the catheter, and advanced to a location inside the artery at the lesion. The stent is then expanded to a larger diameter, by the balloon portion of the catheter, to implant the stent in the artery at the lesion. Typical stents and stent delivery systems are more fully disclosed in U.S. Pat. No. 5,514,154 (Lau et al.), U.S. Pat. No. 5,507,768 (Lau et al.), and U.S. Pat. No. 5,569,295 (Lam et al.).

Stents are commonly designed for long-term implantation within the body lumen. Some stents are designed for non-permanent implantation within the body lumen. By way of example, several stent devices and methods can be found in commonly assigned and common owned U.S. Pat. No. 5,002,560 (Machold et al.), U.S. Pat. No. 5,180,368 (Garrison), and U.S. Pat. No. 5,263,963 (Garrison et al.).

Patients treated by PTCA procedures, even when implanted with stents, however, may suffer from restenosis, the coronary vessel collapsing or becoming obstructed by extensive tissue growth, also known as intimal hyperplasia, at or near the site of the original stenosis. Clinical studies have indicated that anti-proliferative drug therapy or intravascular low-dose radiation therapy after balloon angioplasty or an atherectomy procedure can prevent or reduce the rate of restenosis caused by intimal hyperplasia.

One approach for performing low-dose intravascular radiotherapy is using a treatment catheter with a low-intensity radiation source. Another approach uses a low-intensity implantable radioactive device such as a radioactive stent with either beta emitting or low energy gamma-emitting radioisotopes.

Intravascular or intraductal implantation of a radioactive stent generally involves advancing the stent on a balloon catheter or a similar device to the designated vessel/duct site, properly positioning the stent at the vessel/duct site, and deploying the stent by inflating the balloon which then expands the stent radially against the wall of the vessel/duct. Proper positioning of the stent requires precise placement of the stent at the vessel/duct site to be treated. Visualizing the position and expansion of the stent within a vessel/duct area is usually done using a fluoroscopic or x-ray imaging system.

Generally, the implantable stent is made radioactive prior to being inserted into the patient. To make a stent radioactive, a number of techniques are used in the field. For example, a beta-emitting or low energy gamma-emitting radioisotope may be implanted or alloyed into a metal from which the stent is made. The radioisotope may also be coated onto the surface of the stent using an electroplating process. Furthermore, the stent may be made radioactive through neutron activation in a nuclear reactor or similar facility.

Each of these techniques has certain disadvantages including poor and/or non-uniform adhesion of the radioisotope to the surface of the stent, fabrication difficulties with respect to radiation exposure of workers during the manufacturing process, and the risk of generating considerable quantities of undesired isotopes from the neutron activation process which may continue to affect the irradiated tissue long after the desired restenosis treatment period is over. Another significant shortcoming associated with current methods of making a stent radioactive is that these methods are complex and require the performance of many sequential processing steps, which greatly increase the radioactive stent manufacturing cost.

A requirement for any clinically useful stent is that it should have good visibility under fluoroscopic x-ray illumination so that the position of the stent during the implantation procedure is visible to the physician performing the procedure. Since implantable radioactive stents are generally made of metal or metal alloys such as 316L stainless steel or nickel-titanium alloy, such as nitinol, they are not readily visible under fluoroscopic illumination. To make these, and other, non-radioactive, stents manufactured from non-radiopaque materials visible in an x-ray, radiopaque markers are typically attached onto the stent using a number of techniques. One current technique involves applying a coating of a radiopaque marker material such as gold or tantalum onto the stent, or selected portions of the stent, using an electroplating process. Another technique involves soldering or brazing a radiopaque marker material at specific locations onto the stent. Generally, radiopaque markers are soldered at the longitudinal ends, that is, the most proximal and most distal portions of the stent.

A number of shortcomings or disadvantages are associated with the prior art devices and techniques for attaching radiopaque markers onto radioactive or non-radioactive stents. Other current radiopaque markers that are attached within the surface of the stent may impair the expansion capability of the stent. Another disadvantage with current radiopaque marker technology is that, when viewed under fluoroscopic illumination, the radiopaque markers may provide poor or no indication of whether the stent is fully extended. Another significant shortcoming associated with current methods of attaching a radiopaque marker material onto a radioactive or non-radioactive stent is that these methods can be tedious, imprecise, and require the performance of many sequential processing steps, which greatly increase the stent manufacturing cost. Moreover, deposition techniques such as electroplating or sputter coating of the radiopaque materials may completely and uniformly coat the stent, thus altering the surface of the stent so that tissue and fluids within vessel lumens are exposed to a material other than stainless steel. Further, the coating may crack or fatigue when flexed.

SUMMARY OF THE INVENTION

The invention provides for improved stent designs and methods for depositing a radiopaque material on an implantable medical device, such as a stent. The stents and methods described all provide for the application of radiopacifiers to render the stent or other intraductal medical device radiopaque, either in whole or in part, thus allowing the use of fluoroscopy to assist in placing the stent or medical device at a desired location in the lumen of a vessel or duct.

A stent or intraductal medical device is provided that has a layer of radiopaque material deposited on the surface of the stent. The radiopaque materials to be deposited on the stent or intraductal medical device materials known in the art of radiopaque markers, such as silver, gold, platinum or tantalum, or other materials that are compatible with implantation in a body lumen or duct and which are visible under fluoroscopy or other body vessel/organ imaging system.

In one embodiment, the radiopaque layer may be contiguous over the surface of the stent. In an alternative embodiment, the surface of the stent may be formed having a plurality of cavities, or microdepots, distributed over the outer surface of the stent. Such a stent is rendered opaque by deposition of radiopaque material atoms in the cavities or microdepots. The microdepots may be formed over the entire outer surface of the stent or medical device, or they may be formed in only selected areas of the device, such as in areas adjacent the distal and proximal ends of the device. Even if microdepots are formed over the entire outer surface of the device, the radiopaque materials may be applied to only selected microdepots. For example, radiopaque material may be deposited only in microdepots adjacent the distal and proximal ends of the device. Deposition of radiopaque material in microdepots located on the outer surface of the device is advantageous in that the radiopaque materials are not exposed to the blood or ductal fluid stream flowing through the interior of the stent or medical device. This helps prevent any deleterious effect on the blood or ductal fluid caused by the radiopaque material.

In one embodiment, the radiopaque materials are deposited on the surface of the stent or medical device by dipping or immersing the stent or medical device into a mixture or solution of radiopaque material atoms and a suitable solvent or suspension agent. Such a solution or mixture may include, for example, phosphoric acid, Freon or other solvent. In another approach, the radiopaque material atoms may be suspended in a polymer solution having material characteristics, such as viscosity or wetting properties, that suspend the radiopaque material atoms in the polymer solution while coating the atoms with the polymer.

The radiopaque material atoms may be applied to the surface of the stent or medical device using a variety of methods, such as dipping or immersion. The entire stent or medical device may be dipped or immersed either in whole, or in part. For example, only the areas of the stent or medical device adjacent to the distal and proximal ends of the stent or medical device may be dipped or immersed in the mixture or solution containing the radiopaque material atoms.

Alternatively, where the stent or medical device includes cavities or microdepots formed on the outer surface of the stent or medical device, the mixture or solution containing the radiopaque material atoms may be deposited in the cavities or microdepots using micro-injection. In this method, the mixture or solution containing the radiopaque material atoms is injected into the cavities or microdepots covering the outer surface of the stent or medical device, or the atoms may be injected into cavities or microdepots in selected areas of the stent or medical device.

When the radiopaque material solution or mixture has coated the stent or medical device, excess radiopaque material solution or mixture may be removed from the stent or medical device by centrifuging or shaking the stent or medical device. Centrifuging is particularly advantageous where the radiopaque material atoms have been deposited on a stent or medical device having cavities or microdepots, since the centrifugal force operating on the device while being centrifuged assists distribution of the radiopaque solution across the device. Moreover, the solution stripped from the stent or medical device may be recycled and reused, thus minimizing loss of material and reducing cost.

In another embodiment of the present invention, the coated stent or medical device may be heated to remove excess solvent or solution and/or to bind the radiopaque material atoms on the surface of the stent or medical device. The heating process may be accomplished using various methods of applying heat in a controlled manner to the coated stent or medical device, such as using a thermal oven, an inert gas plasma, exposing the coated device to an electric arc, or by subjecting the radiopaque atoms coating the stent or medical device to low power exposure from an excimer or other suitable laser.

Where high power, high temperature processes are used to remove excess solvent or solution, the polymer in the mixture may be selected so that it completely incinerates into volatile combustion products during the heating process. Polymers such as polyurethanes and polyolefins, and other suitable polymers, that combust completely at temperatures in the range of 600 to 1000 degrees centigrade could thus be removed from the surface of the stent or medical device, leaving little or no residue.

In yet another embodiment of the present invention, the radiopaque material atoms may be deposited on the surface of the stent or medical device using an electrodeposition process. In this embodiment, the stent or medical device is attached to a cathode or negative terminal of an electrical current source and dipped or immersed into a positively charged ion mixture or solution of radiopaque material atoms. When current flow is initiated, the ions are attracted to the cathode and coat the surface of the stent or medical device.

Other features and advantages of the present invention will become more apparent from the following detailed description, taken in conjunction with the accompanying drawings, which illustrate, by way of example, the principles of the invention.

DETAILED DESCRIPTION OF THE PREFERRED EMBODIMENTS

The present invention provides a radioactive or non-radioactive stent or intraductal implant device having radiopaque material deposited or affixed to the body of the stent such that the radioactive stent is visible under fluoroscopic illumination. Also provided is a method for depositing and affixing radiopacifiers onto such stents or intraductal implant devices.

In the following detailed description, numerous specific details are set forth in order to provide a more thorough understanding of the present invention. However, it will be apparent to those skilled in the art to which this invention pertains that the present invention may be practiced without these specific details. In other instances, well-known devices, methods, procedures, and individual components have not been described in detail so as not to obscure aspects of the present invention.

Figure 1:
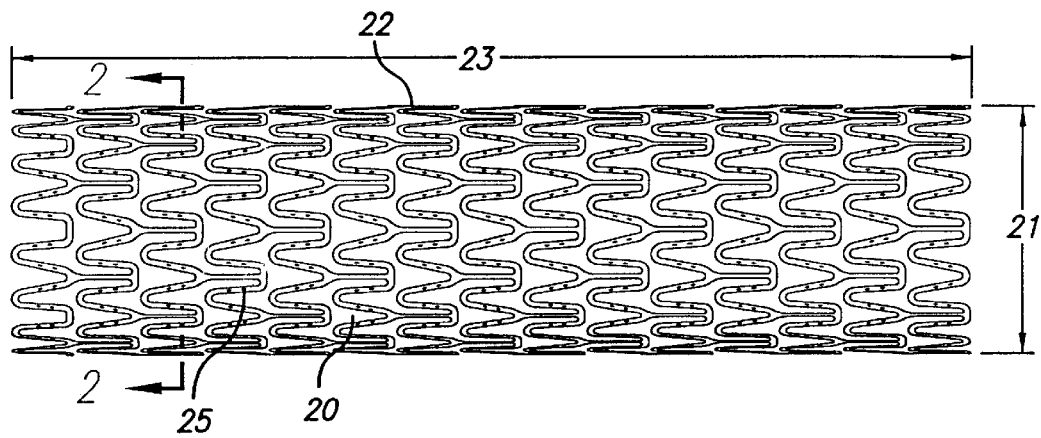
FIG. 1 illustrates a radiopaque stent manufactured according to the method of this invention.

FIG. 1 illustrates an embodiment of an implantable medical device, such as a stent 20, practicing the invention. Generally, stent 20 is a thin-walled cylindrically shaped structure having an expanded or extended diameter 21, an outer surface 22, and a longitudinal length 23. In one embodiment, stent 20 includes a plurality of cavities or "microdepots" 25 disposed on the outer surface 22 of the stent.

Figure 2:
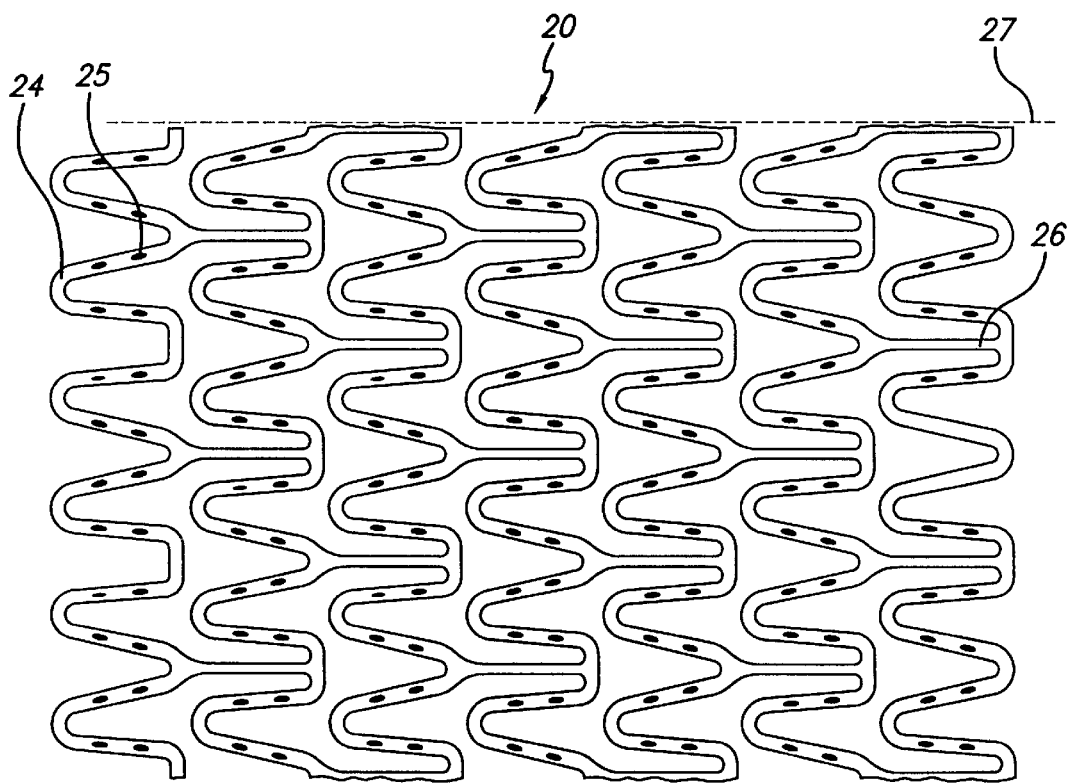
FIG. 2 shows a flat two-dimensional section detail of the radiopaque stent of FIG. 1.

FIG. 2 illustrates a detailed two-dimensional view of the flexible stent 20 of FIG. 1 at 2—2. While stent 20 may include any number of configurations, one desired stent embodiment includes a cylindrical mesh having a plurality of undulating cylindrical elements or rings 24 which are interconnected with one or more connecting elements or links 26 such that the undulating cylindrical elements are generally aligned on a common longitudinal axis 27. The cavities or microdepots 25 disposed on the stent may have a frustum (truncated cone) configuration with a low open surface to pore volume ratio. Microdepots 25 may include various other geometries depending on the type of material, such as, for example, a radioisotope, anti-platelet drug, or radiopacificer material, to be deposited on the stent, the type of medical application the stent will be used for, and the stent manufacturing preferences.

The stent 20 is desired to be implantable and may be made of any material known in the field of stent procedure therapy including metal or metal alloys such as titanium, 316L stainless steel, and nitinol. Alternatively, a non-metal material such as polymer-type, ceramic; or a composition thereof may be used to form the stent. The stent may also be formed from a material or materials resulting in a radioactive stent.

Depending on the type of use, the length 23 of the stent 20 may be in the range of approximately 5 to 100+ mm for vascular stents. For stents used in procedures to inhibit the proliferation of tumor neoplasma in ductal organs, the length 23 of the radioactive stent may be in the range of approximately 5 mm to 30 cm.

When deployed in their extended or expanded configuration, vascular stents typically have an expanded diameter 21 in the range of approximately 2 to 12 mm. For stents used in procedures to inhibit the proliferation of tumor neoplasma in ductal organs, the expanded diameter 21 of the stent 20 is generally in the range of approximately 2 mm to 4 cm.

It should be noted that although this invention is described using a stent as an example of an implantable device, this invention is not limited only to stents or stent-like devices. This invention can be practiced using other implantable medical devices, such as, for example implantable grafts.

Figure 3:
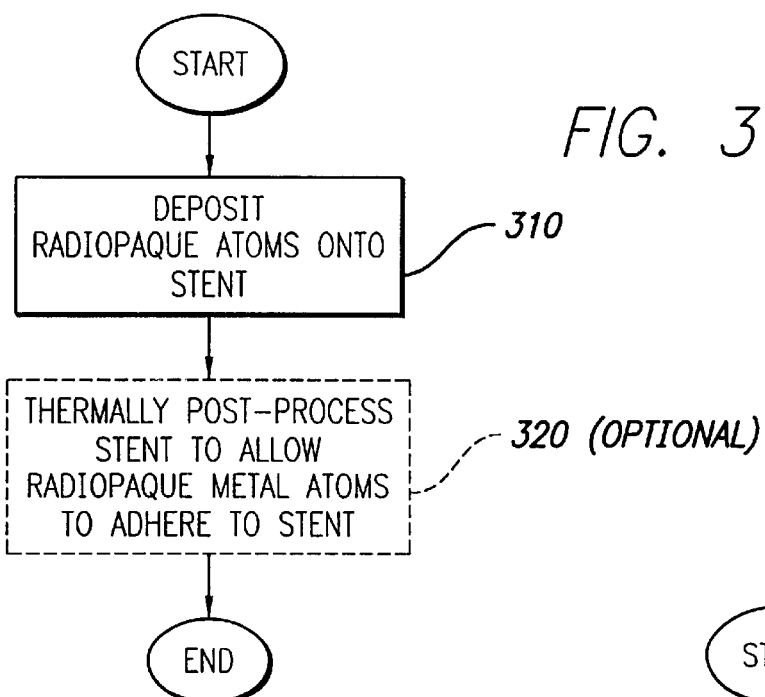
FIG. 3 is a flow chart illustrating the major steps of one embodiment of he method of this invention.

FIG. 3 is a flow chart illustrating the major steps of one embodiment of the method of the present invention. In this embodiment the method begins by depositing, or loading, radiopaque atoms onto an implantable medical device such as a stent in step 310. The atoms may be deposited on the entire outer surface 22 of the stent, or preferably within the microdepots 25 of stent 20. The deposition of radiopaque atoms on the stent or implantable device is generally achieved by depositing the atoms as part of a mixture or solution using a number of processes such as dip-coating, which may be followed by a centrifugation or a shaking action, electrodeposition, sputtering, micro-injection, thin-film spray coating, ion beam assisted deposition (IBAD), or a combination thereof.

Low-intensity implantable radioactive stents manufactured using an embodiment of the present invention generally employ beta-emitting or low energy gamma-emitting radioisotopes. A beta-emitter radioisotope, such as phosphorus-32 ($p^{32}$), which emits low-energy, short half-life beta particles, is typically desired to provide optimum therapeutic treatment with maximum patient safety. The list of possible beta emitting and low-penetration gamma-emitting radioisotopes includes, but is not limited to, $Sn^{123}$, $Sr^{89}$, $p^{33}$, $Pd^{103}$, and $I^{125}$. Other types of treatments, such as treatment to inhibit proliferation of tumor neoplasma in ductal organs, such as the kidney, pancreas, liver and esophagus, may require a more penetrating gamma-emitting radioisotope such as $Ir^{192}$, $Co^{57}$, $Rh_{106}$ and $Tc^{99}$.

The radiopaque marker materials to be deposited on the stent may include any materials known in the art of radiopaque markers, such as silver, gold, platinum, or tantalum, that allow markers to become visible under fluoroscopy or other body vessel/organ imaging system.

Referring again to FIG. 3, in one embodiment, the radiopaque atoms, following deposition onto the stent, undergo a heating process that causes the radiopaque atoms to adhere to the stent, as illustrated by step 320. During step 320, the radiopaque atoms are heated to a temperature high enough so that they soften and adhere, or bond, to the surface 22 of the stent 20 or onto the inner surface of the microdepots 25. During the heating process, the temperature of the radiopaque metal atoms is raised to a temperature that is in the range of approximately 200 to 900 degrees Celsius. The radiopaque metal atoms are maintained at this temperature for a time period that is in the range of approximately 1 minute to 3 hours. The heating process may be performed using any techniques and devices known in the art, including, for example, thermal processing, inert gas plasma processing, electric arc processing, an excimer laser exposure at low power, or any laser that uses a noble-gas halide to generate radiation usually in the ultraviolet region of the spectrum.

Figure 4:
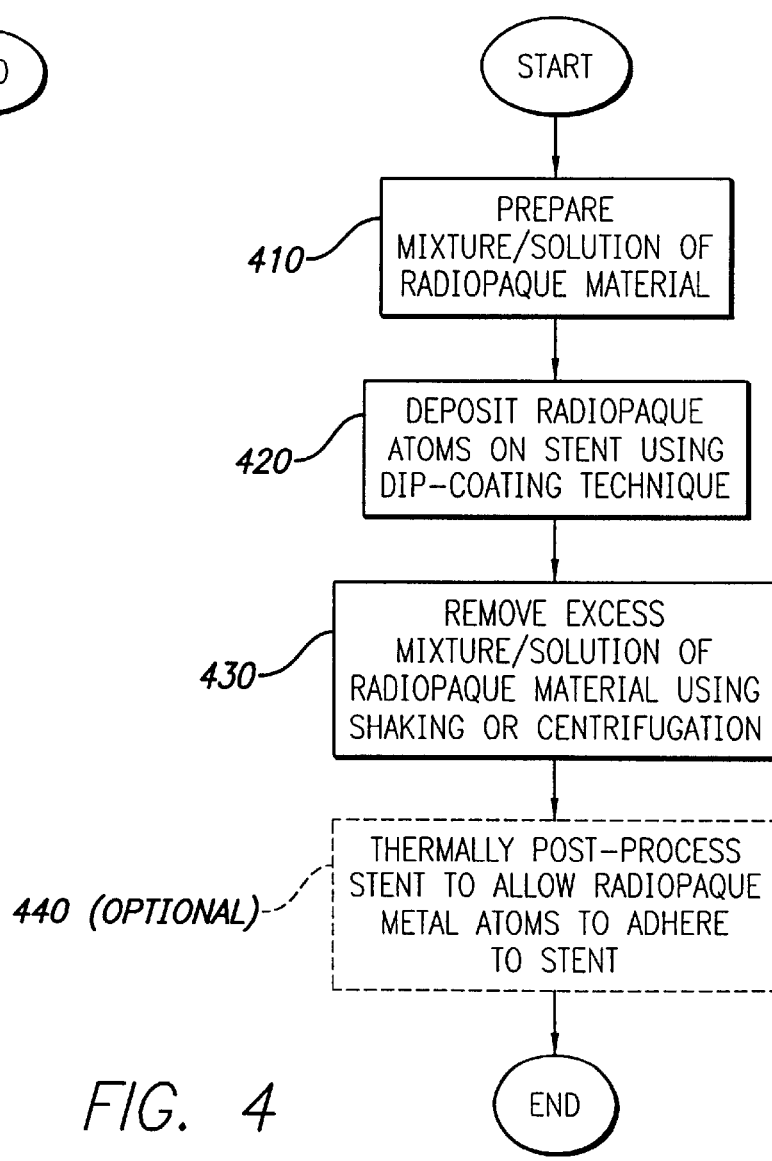
FIG. 4 is a flow chart illustrating the major steps of another embodiment of the method of this invention.

Referring now to FIG. 4, in another embodiment of the present invention, radiopaque atoms may be deposited or loaded onto the surface 22 of stent 20. Alternatively, the radiopaque atoms and radioisotopes may be deposited onto cavities or microdepots 25 if such cavities or microdepots are configured on the stent.

In this embodiment, deposition of the radiopaque atoms begins at step 410 by preparing a mixture or solution of radiopaque material atoms. In one variation of this embodiment, radiopaque metal atoms such as gold (Au) are suspended or dissolved in an aqueous solution of phosphoric acid $H_3P^{32}O_4$. In another approach, the radiopaque metal atoms may be suspended in a polymer solution. The material characteristics of the polymer solution, such as, for example, the viscosity of the polymer solution, enables the radiopaque atoms to become coated with the polymer. Examples of suitable polymers include polybutlymethacrylate (PBMA), polymethlymethacrylate (PMMA), polyethylene glycol-5000 (PEG-5000) and ethylene vinyl alcohol (EVAL).

At step 420, the mixture of radiopaque material atoms is applied or deposited onto the stent 20. In one approach, the mixture is applied onto the stent by immersing the stent in the aqueous solution of phosphorous acid $H_2P^{22}O_4$ containing the radiopaque metal atoms by dipping the stent into the solution. Stent 20 is immersed in the aqueous solution of phosphorous acid $H_3P^{32}O_4$ for a time period that is in the range of approximately 1 second to 5 minutes. During this immersion or dipping, the radiopaque metal atoms coat the structure of the stent.

Alternatively, at step 420, radiopaque atoms may be suspended in a highly wetting solvent such as Freon™, THF (Tetra Hydrofuran), or the like. Other suitable solvents include toluene, cyclohexanone, dimethly acetamide (DMAc) and Methoxopropanol acetate (PM acetate).

In one embodiment, radiopaque atoms are mixed into a solution containing thirty-five percent (35%) cyclohexanone and sixty-three percent (63%) dimethyl acetamide by weight. Thus, the radiopaque atoms comprise two percent (2%) by weight of the mixture or solution. Alternatively, the concentration of radiopaque atoms in the mixture or solution may be in the range of one to fifty percent (1%–50%) by weight, with the concentrations of the solvent and/or polymer adjusted accordingly to provide a mixture or solution having properties suitable for application of the mixture or solution to the stent or medical device.

In one alternative embodiment, the mixture of radiopaque material atoms, which may also contain a polymer, is applied onto stent 20 by dipping or immersing the stent into the Freon or solvent solution for a time period that is in the range of approximately 1 second to 5 minutes such that the radiopaque metal atoms are deposited onto the structure of the stent by capillary action.

At step 430, the coated or loaded stent is removed from the mixture or solution and is then subjected to vigorous and/or rapid movement. This rapid movement of the stent acts to remove any excess mixture or solution containing the radiopaque material atoms from the surface 22 of the stent and/or from the stent's cavities or microdepots 25.

In one embodiment, step 430 is performed by subjecting the coated stent to centrifugation action. In this embodiment, the stent is mounted onto a mandrel and is spun at a rotational speed in the range of approximately 3000 to 7000 rotations per minute (rpm) for a time period that is in the range of approximately 1 to 3 minutes. For a stent without cavities or microdepots on the stent surface, the centrifugation step 430 may be controlled to remove excess radiopaque material mixture or solution while leaving a coating of radiopaque metal atoms deposited on the surface of the stent of a desired thickness. When processing a stent 20 having cavities or microdepots 25, the centrifugation step 430 may be adjusted by increasing or decreasing the rotational speed of the mandrel such that the radiopaque material deposited in the microdepots, as well as on the stent surface, achieves a desired thickness.

One advantage of suspending the radiopaque material atoms in a mixture or solution containing a polymer to deposit the radiopaque material atoms on the surface of a stent 20 employing microdepots 25, such as the stent illustrated in FIGS. 1 and 2, is that the centrifugation step 430 generally removes most or all the mixture or solution of radiopaque metal atoms present in areas other then the microdepots. This result is due in part because the radiopaque metal atoms inside the microdepots are embedded in the viscous polymer material within the volume of the microdepot, and are thus removed at a slower rate than the atoms coating the outer surface of the stent. Thus, the polymer present in the mixture or solution acts as binder for the atoms deposited within the microdepot.

In another embodiment of the method employing step 430, the removal of excess radiopaque metal atoms solution or mixture from the surface of the stent is achieved by subjecting the stent to a shaking-like motion.

It should be noted that the processing times for keeping the stent immersed into the solution containing the radiopaque atoms, $t_{dipping\ stent}$, or for rapidly moving or shaking the stent, $t_{shaking\ stent}$, or centrifuging (i.e., spinning) stent 20 in the centrifugation chamber, $t_{centrifuge\ stent}$, may vary considerably from the times provided in the above exemplary embodiment. These processing times may be modified to take into consideration the type or design of the stent used, such as, for example, the processing time for a cylindrical mesh wire stent may be either shorter or longer that the time required to process a cylindrical solid metal stent or a stent having microdepots on its surface. Moreover, the type of aqueous solution or mixture used to apply the radiopaque material may also alter the immersion and/or shaking or spinning times.

Referring again to FIG. 4, following the deposition of the radiopaque mixture/solution onto the stent and/or its microdepots and removal of excess solution from the stent, the stent 20 may be thermally post-processed to allow the radiopaque metal atoms to adhere to the stent. It will be understood by those skilled in the art that such thermal post-processing will only be required by certain mixtures and solutions to promote adherence of the radiopaque atoms to the surface of the stent. Depending on the solutions used, post processing may not be required.

In one embodiment, as part of step 440, the radiopaque metal atoms may be heated to a point such that they soften and form a coherent mass that is masked inside microdepots 25. During this process, the temperature of the radiopaque metal atoms is raised to a temperature that is in the range of approximately 200 to 900 degrees Celsius. The radiopaque metal atoms are maintained at this temperature for a time period that is in the range of approximately 1 minute to 3 hours.

The thermal post-processing step 440 may be performed using any techniques and devices known in the art of metal processing. The choice of the heating process technique used depends on a number of variables such as the type of process employed to deposit the radiopaque atoms on the stent (i.e., dip-coating plus centrifugation, electroplating, ion implantation, spay coating), manufacturing preferences such as ease, cost and complexity and other variables.

In one embodiment, heating process step 440 may be accomplished using a thermal processing approach. In another embodiment, heating process step 440 may be accomplished using an inert gas plasma processing approach where the power for the plasma cycle is modified to allow the opaque material atoms such as gold to soften and stabilize themselves within the microdepots 25. In yet another embodiment, heating process step 440 may be achieved by subjecting the radiopaque atoms to low power exposure from an excimer laser which typically uses a noble-gas halide to generate radiation usually in the ultraviolet region of the spectrum. In yet another embodiment, heating process step 440 may be accomplished by subjecting the radiopaque metal atoms to heat from an electric arc.

Where high power, high temperature processes are used to remove excess solvent or solution, the polymer in the mixture may be selected so that it completely incinerates into volatile combustion products during the heating process. Polymers such as polyurethanes and polyolefins, and other suitable polymers, that combust completely at temperatures in the range of 600 to 1000 degrees centigrade could thus be removed from the surface of the stent or medical device, leaving little or no residue.

It should be noted that step 440 is not required to practice the invention. For example, where the radiopaque metal atoms are in a polymer-like solution that is used to coat a stent having microdepots or cavities, the excess solution may be removed from the stent and the stent allowed to air-dry for a specific period of time. As the solvent or like material dries out, the radiopaque atoms remain embedded in the polymer inside the volume of the microdepots.

Depositing or loading radiopaque metal atoms onto microdepot-patterned stents and using centrifugation to remove excess solution has a number of advantages. First, the centrifugal force helps redistribute the solution fluid flow around the cylindrical elements or rings and connecting elements or links of the stent. The method may be performed using a semi-automated manufacturing mode, thus reducing manufacturing times and costs. The radiopaque solution that strips off the stent can be recycled and reused, thus minimizing loss of material and reducing cost. Biomedical devices other than stents, for example implantable grafts, may also be coated by this method.

Figure 5:
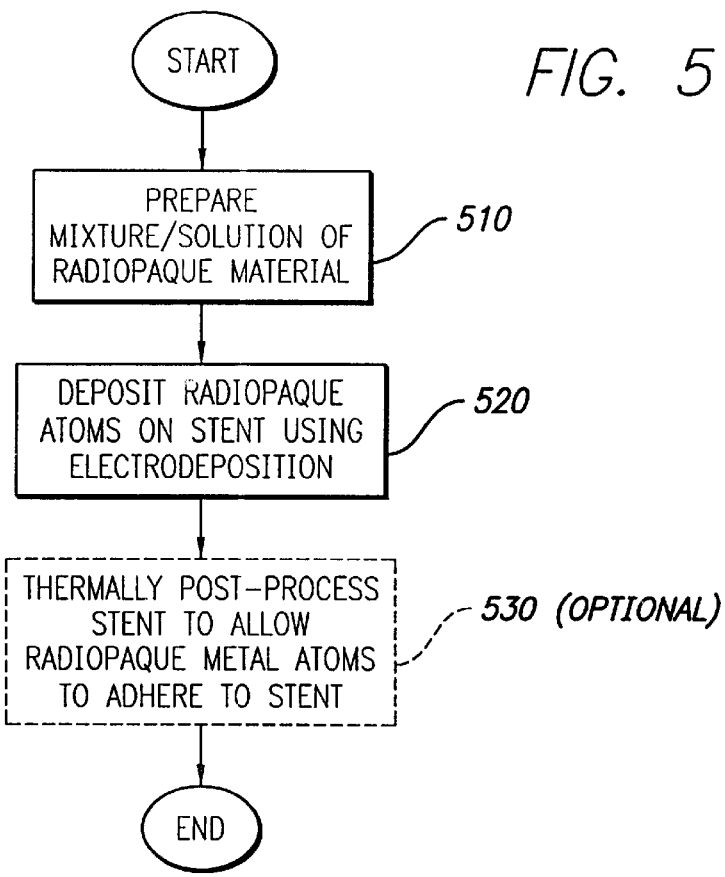
FIG. 5 is a flow chart illustrating the major steps of yet another embodiment of the method of this invention.

Referring now to FIG. 5, in another embodiment of the method of this invention, radiopaque atoms are deposited or loaded onto the stent 20 using an electrodeposition process. As part of the electrodeposition process, radiopaque atoms of metal such as gold (Au) are deposited by electrochemical deposition of Au through faradic current flux.

The method of this embodiment begins at step 510 by preparing a positively charged ion mixture or solution of radiopaque material atoms. In one approach, radiopaque metal atoms, such as gold (Au), are suspended or dissolved in an aqueous solution of phosphoric acid $H_3P^{32}O_4$. Alternatively, at step 510, the radiopaque atoms can be suspended in a highly wetting solvent such as Freon™, THF (Tetra Hydrofuran), or the like.

The stent is connected to the cathode or negative terminal of an electrical current source at step 520 while the anode or positive electric terminal of a source is connected to a mandrel or similar device that is dipped into the positively charged ion solution of radiopaque metal atoms. The ions are attracted to the cathode and the coating is deposited on the surface of the stent. The thickness of the layer of deposited radiopaque metal atoms depends on the amperage of the electric current, the concentration of the radiopaque metal ions, the length of time that the stent is subjected to the faradic current coating cycle, as well as other electroplating process characteristics known in the art. For a stent having cavities or microdepots 25 on its surface, the thickness of the layer of deposited radiopaque metal atoms also depends on the particular size and geometrical shape of microdepots 25. It is generally desired to have the thickness of the layer "masked" or flat within the microdepot.

Referring again to FIG. 5, following the deposition of radiopaque metal atoms using the electrodeposition process, the stent 20 may be thermally post-processed to allow the radiopaque metal atoms to adhere to the stent as is described in step 530. This heating process 530 is similar to the process discussed above with reference to step 440 of FIG. 4. This step may be followed by the deposition of other materials, such as, for example, sequential administration of a designed-to-coat blood compatible substance.

In one embodiment, heating process step 530 may be accomplished using a thermal processing approach. In another embodiment, heating process step 530 may be accomplished using an inert gas plasma processing approach where the power for the plasma cycle may be modified to allow the opaque material atoms, such as gold, to soften and stabilize themselves on the surface of stent 20 or within the microdepots 25. In yet another embodiment, heating process step 530 may be accomplished by subjecting the radiopaque atoms to low power exposure from an excimer laser which typically uses a noble-gas halide to generate radiation usually in the ultraviolet region of the spectrum. In yet another embodiment, heating process step 530 may be accomplished by subjecting the radiopaque metal atoms to heat from an electric arc.

During the heating process, the temperature of the radiopaque metal atoms is raised to a temperature that is in the range of approximately 200 to 900 degrees Celsius. The radiopaque metal atoms are maintained at this temperature for a time period of 1 minute to 3 hours.

As stated previously with reference to step 430 of FIG. 4, step 530 is not required to practice the invention. For stents with microdepots or cavities that are coated with a polymer or polymer-like solution containing radiopaque metal atoms, the stent may be allowed to air-dry for a specific period of time instead of heating. As the aqueous solution or solvent or like material dries out, the radiopaque atoms remain embedded in the polymer inside the volume of the microdepots. Therefore, heating the radiopaque atoms to cause them to adhere to the stent as set forth in step 530 may not be necessary in order to obtain a radiopaque stent.

Figure 6:
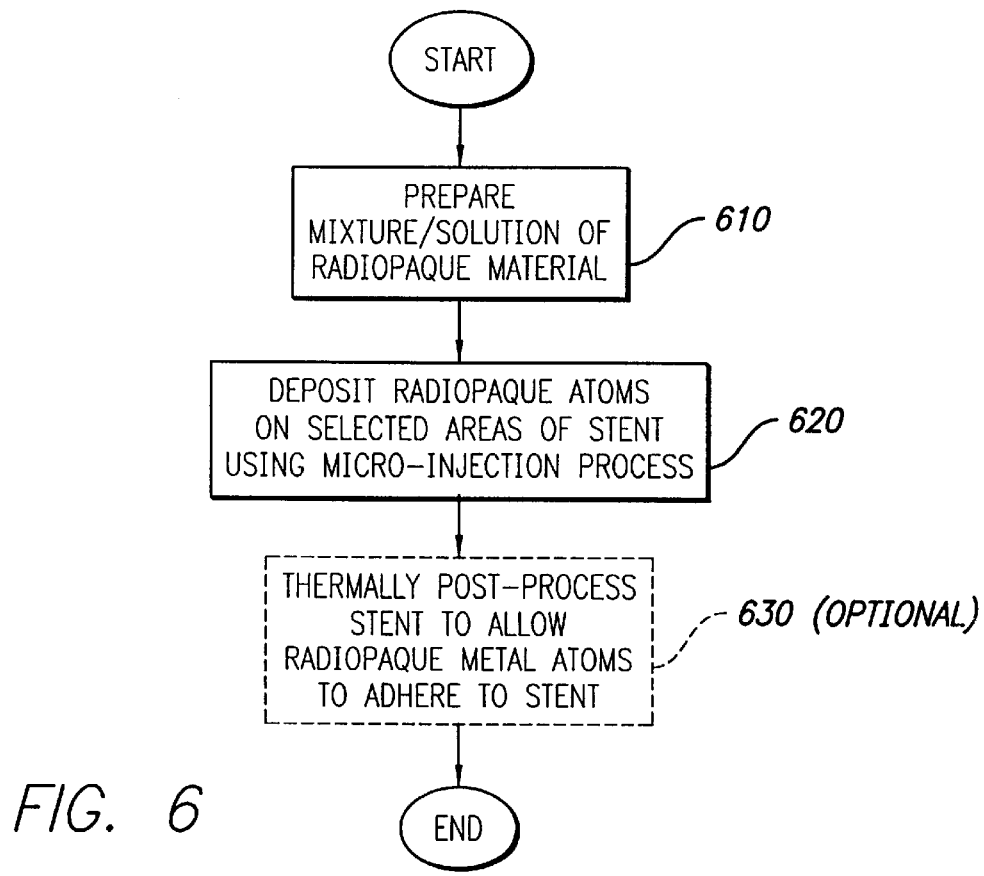
FIG. 6 is a flow chart illustrating the major steps of still further embodiment of the method of this invention.

Referring now to FIG. 6, in yet another embodiment of the method of the invention, radiopaque atoms are deposited or loaded inside depots 25 using a micro-injection process. The method of this embodiment begins at step 610 by preparing a mixture or solution of radiopaque material atoms. In one approach, radiopaque metal atoms such as gold (Au) are suspended or dissolved in an aqueous solution of phosphoric acid $H_3P^{32}O_4$. Alternatively, the radiopaque metal atoms may be suspended in a highly wetting solvent such as Freon™, THF (Tetra Hydrofuran), or the like.

The stent is mounted on a mandrel or similar device and placed in a chamber-like enclosure at step 620. The radiopaque solution prepared during step 610 is then injected onto the stent using a micro-injector system. If a microdepot-patterned stent is used, the radiopaque solution may be injected into a plurality of microdepots 25. The micro-injection process may deposit the radiopaque solution into all microdepots or only into a specific combination of micro-depots such as those positioned adjacent the proximal and distal ends on the stent. The micro-injection process may be performed manually, automatically, or semi-automatically.

Following the radiopaque metal atom deposition using the micro-injection process in step 620, the stent 20 may be post-processed using a heating or similar technique to allow the radiopaque metal atoms to adhere to the stent in step 630. The heating process step 630 is similar to the heating process described above with reference to step 440 in FIG. 4.

In one variation of this embodiment, heating process step 630 may be achieved using a thermal processing approach. In another embodiment, heating process step 630 may be accomplished using an inert gas plasma processing approach where the power for the plasma cycle is modified to allow opaque material atoms such as gold to soften and stabilize themselves on the surface of the stent 20 or within microdepots 25. In yet another embodiment, heating process step 630 may be accomplished by subjecting the radiopaque atoms to low power exposure from an excimer laser which uses a noble-gas halide to generate radiation usually in the ultraviolet region of the spectrum. In yet another embodiment, heating process step 630 may be accomplished by subjecting the radiopaque metal atoms to heat from an electric arc.

During the heating process of step 630, the temperature of the radiopaque metal atoms may be raised to a temperature that is in the range of approximately 200 to 900 degrees Celsius. The radiopaque metal atoms are maintained at this temperature for a time period of 1 minute to 3 hours.

Where high power, high temperature processes are used to remove excess solvent or solution, the polymer in the mixture may be selected so that it completely incinerates into volatile combustion products during the heating process. Polymers such as polyurethanes and polyolefins, and other suitable polymers, that combust completely at temperatures in the range of 600 to 1000 degrees centigrade could thus be removed from the surface of the stent or medical device, leaving little or no residue.

In yet another embodiment, the mixture containing a polymer as described above and radiopaque atoms is deposited on the stent or medical device using any of the procedures previously described. The stent or medical device is then heated to a temperature sufficient to soften the radiopaque atoms and allow those atoms to adhere to the surface of the stent or medical device. The temperature is also high enough to incinerate the polymer and thus remove it from the surface. In this manner, only the radiopaque atoms remain on the surface of the stent or medical device, and, because of the high temperature used, are sintered to the surface of the stent or medical device. Heating the stent or medical device to a temperature in the range of 600 to 1000 degrees Celsius will incinerate the polymer and sinter the radioactive atoms to the surface of the stent or medical device.

As discussed previously, it should be noted that step 630 is not required to practice the invention. For stents with microdepots or cavities that are coated with a polymer-like solution or mixture containing radiopaque metal atoms, the stent may just be allowed to air-dry for a specific period of time rather than exposing the stent and dried solution to heat. As the aqueous solution or solvent or like material dries out, the radiopaque atoms remain embedded in the polymer inside the volume of the microdepots. Therefore, heating the radiopaque atoms to cause them to adhere to the stent as described in step 630 may not be necessary in order to obtain a radiopaque stent.

The radiopaque stent or implantable medical device manufactured using the methods described herein will be completed with much higher regional radiopacity for the same amount of radiopaque material loading averaged over the total surface area of the stent. One advantage of this method of providing a radiopaque stent is that radiopaque materials can be loaded inside the microdepots and co-processed simultaneously with radioactive isotopes to yield a final stent or implantable medical device that is both radioactive and either radiopaque in its entirety or at selected locations on the stent or device.

The method of this invention is especially well suited for use on implantable medical devices, such as stents, having a microdepot-like pattern disposed on their surface since there is no need to deposit the radiopaque mixture over the entire contour of the stent in order to obtain visualization of the entire stent under fluoroscopy. Furthermore, by applying the method of this invention to a microdepot-patterned stent, the various negative effects associated with gold coating and the way it interacts with blood cells can be minimized or eliminated. Since the radiopaque material is deposited and affixed only within the volume of the microdepots, that is, positioned on the outer surface of the stent, there is very limited or no physical contact between the blood flow in the inner lumen of the stent and the radiopaque material.

While several specific embodiments of the invention have been illustrated and described, it will be apparent that various modifications can be made without departing from the spirit and scope of the invention. Accordingly, it is not intended that the invention be limited, except as by the appended claims.

What is claimed:

1. A method comprising:
   providing an implantable medical device with a plurality of cavities disposed on the outer surface of the device; and
   depositing into and retaining radiopaque material in the plurality of cavities to make the device radiopaque.

2. The method of claim 1, wherein depositing comprises:
   applying a mixture comprising the radiopaque material onto the device so as to coat at least a portion of the plurality of cavities with the mixture; and
   removing an excess quantity of the mixture from the device such that a layer of the mixture is formed in the cavities.

3. The method of claim 2, further comprising preparing the mixture by suspending the radiopaque material in a solution prior to applying the mixture onto the device.

4. The method of claim 2, further comprising preparing the mixture by dissolving the radiopaque material in a solution prior to applying the mixture onto the device.

5. The method of claim 2, wherein applying a mixture comprises immersing at least a portion of the device into the mixture.

6. The method of claim 2, wherein removing excess radiopaque material includes centrifuging the device.

7. The method of claim 2, wherein removing the excess radiopaque material includes shaking the device.

8. The method of claim 1, further comprising affixing the radiopaque material to the device by heating the material to a selected temperature to allow the radiopaque material to bond to the device.

9. The method of claim 1 further comprises affixing the radiopaque material onto the device by drying the material such that the radiopaque material bonds to the device.

10. The method of claim 2, wherein the mixture includes a polymer.

11. The method of claim 1, wherein the radiopaque material is a metal selected from the group of metals consisting of gold, platinum, silver, and tantalum.

12. The method of claim 1, wherein the implantable medical device is a stent.

13. The method of claim 1, wherein depositing a radiopaque material on the device is accomplished using an electrodeposition process.

14. The method of claim 13, wherein depositing comprises:

connecting the device to a cathode of an electrical source;

connecting a mandrel to an anode of an electrical source;

immersing at least a portion of the device in a positively-charged ion mixture comprising the radiopaque material; and applying an electrical current to the device so as to deposit a layer of the positively-charged ion mixture onto at least a portion of the device.

15. The method of claim 14, further comprising preparing the positively-charged ion mixture prior to immersing at least a portion of the device in the positively-charged ion mixture.

16. The method of claim 14, wherein the radiopaque material in the positively-charged ion mixture is a metal selected from the group of metals consisting of gold, platinum, silver, and tantalum.

17. The method of claim 1, wherein depositing a radiopaque material on the device is accomplished using a micro-injection process.

18. The method of claim 17, further comprising preparing a mixture containing the radiopaque material prior to injecting the mixture into the cavity.

19. The method of claim 17, wherein the radiopaque material is a metal selected from the group of metals consisting of gold, platinum, silver, and tantalum.

20. The method of claim 17, wherein depositing is performed on a stent.

21. The method of claim 8, wherein heating the material comprises heating the radiopaque material to a selected temperature using a gas plasma process so as to cause the radiopaque material to soften and affix onto the device.

22. The method of claim 21, wherein the selected temperature is in a range of approximately 200 to 900 degrees Celsius.

23. The method of claim 22, wherein the gas plasma process uses an inert gas selected from the group of inert gases consisting of argon, helium, neon, krypton and xenon.

24. The method of claim 8, wherein heating the material comprises heating the radiopaque material to a selected temperature using a laser beam light so as to cause the radiopaque material to soften and affix onto the device.

25. The method of claim 24, wherein the selected temperature is in a range of approximately 200 to 900 degrees Celsius.

26. The method of claim 8, wherein heating the material comprises heating the radiopaque material to a selected temperature using an electric arc device so as to cause the radiopaque material to soften and affix onto the device.

27. The method of claim 26, wherein the selected temperature is in a range of approximately 200 to 900 degrees Celsius.

28. The method of claim 2, wherein the layer has a thickness in a range of approximately 1 to 50 μm.

29. A stent, comprising:

a plurality of cylindrical elements which are interconnected so as to be generally aligned on a common longitudinal axis;

at least one connecting element for interconnecting the plurality of cylindrical elements;

a plurality of cavities disposed on the outer surface of the plurality of cylindrical elements; and a radiopaque coating affixed in the plurality of cavities in which the coating is formed by deposition of a radiopaque material.

30. The stent of claim 29, wherein the stent is made of a material selected from the group consisting of metal, polymers, and ceramics.

* * * * *